United States Patent [19]

Keller

[11] 4,109,646

[45] Aug. 29, 1978

[54] AUTOMATIC BLOOD PRESSURE CUFF APPLICATOR

[75] Inventor: Robert B. Keller, Ann Arbor, Mich.

[73] Assignee: Weisman & Allen, Madison Heights, Mich.

[21] Appl. No.: 752,567

[22] Filed: Dec. 20, 1976

[51] Int. Cl.² .............................................. A61B 5/02
[52] U.S. Cl. .......................... 128/2.05 C; 128/2.05 M
[58] Field of Search .................... 128/2.05 C, 2.05 A, 128/2.05 G, 2.05 M, 327

[56] References Cited

U.S. PATENT DOCUMENTS

| | | | |
|---|---|---|---|
| 2,352,875 | 7/1944 | Williams et al. | 128/2.05 A |
| 3,757,772 | 9/1973 | Goldblat et al. | 128/2.05 C |
| 3,935,984 | 2/1976 | Lichowsky et al. | 128/2.05 C |
| 3,968,788 | 7/1976 | Hopkins | 128/2.05 C |

FOREIGN PATENT DOCUMENTS 832,560  9/1938  France ............................... 128/2.05 G

*Primary Examiner*—Lee S. Cohen
*Attorney, Agent, or Firm*—Krass & Young

[57] ABSTRACT

An arrangement is disclosed for automatically applying to a body member a flexible inflatable cuff of the type used in taking blood pressure measurements. The arrangement includes a rotatable drum supported between a pair of end plates which have openings formed therein allowing the body member of the subject to pass through the interior of the rotatable drum. A cuff is positioned within the drum in an extended or unwound position, with one end thereof restrained against movement with the drum by virtue of a pair of ties secured to the respective end plates and also to one end of the cuff while the other end of the cuff is adapted to be carried with the drum during rotation thereof by virtue of a flexible element connected to the other end of the cuff and passing through the drum wall and about the periphery thereof with a garter spring connected both to the flexible element and to the drum outer surface. Rotation of the drum produces encirclement of the subject's body member with the garter spring allowing extension of the flexible element into the interior of the drum as the cuff is wound onto the body member with a pressure sensitive securement provided to secure the lapped cuff ends together upon rotation of the drum sufficiently to produce such overlap. Reverse rotation of the drum releases the securement and unwinds the cuff.

19 Claims, 6 Drawing Figures

AUTOMATIC BLOOD PRESSURE CUFF APPLICATOR

BACKGROUND OF THE INVENTION

1. Field of the Invention

This invention concerns blood pressure measurements of the sort involving the application of an occluding cuff to an extremity of the subject in which the blood pressure measurement is to be performed and more particularly concerns apparatus for automatically accomplishing such cuff application.

2. Description of the Prior Art

Due to the widespread incidence of blood pressure abnormalities, particularly high blood pressure, in the population at large and due to the insidious onset of such abnormalities and their potentially highly destructive effects on the health of the afflicted individual, it has been heretofore seen as highly desirable that some mass screening system should be devised so as to enable regular and widespread monitoring of the blood pressure conditions of members of the populace. Automation of the testing procedure has been seen as desirable since traditional clinical methods of performing such measurements involve substantial time expenditure by skilled personnel such as doctors, nurses and other clinicians. The performance of such blood pressure measurements involve a fairly sophisticated technique of inflating an occluding pressure cuff encircling an extremity of the subject, usually the upper arm, with a stethoscope used to listen to the blood flow in the arteries downstream of the occluding pressure cuff. The pressure cuff is initially inflated sufficiently to totally block blood flow to the extremity remote from the point of application of the cuff, and the cuff pressure is subsequently allowed to decline gradually to a point wherein unrestricted blood flow can occur. The clinician by utilizing the stethoscope is able to detect certain characteristic sounds (referred to as "Korotkoff sounds") occurring at cuff pressures corresponding to systolic and diastolic pressure points, in order to determine these pressure values.

Many efforts have been exerted to automate the detection of such systolic and diastolic pressure points in conjunction with an inflatable cuff of the type described. Copending Patent application Ser. No. 714,097, filed Aug. 13, 1976, discloses one such arrangement.

One aspect of such automated methods is that the data so obtained must correspond to the body of clinical data which has been assembled in the past in the carrying out of traditional measurements since such clinical data forms the basis for detection of abnormalities.

Incidental to such automated processes, it would be desirable that the application of the cuff be automated as is the systolic-diastolic pressure point detection function. Most desirably, in carrying out the tests, the subject would merely have to position his wrist, arm, etc., within an opening and the occluding pressure cuff would be automatically applied and pressurized in order to carry out the blood pressure measurement, in the interests of speed and accuracy.

As mentioned above the automation of the process would most desirably closely resemble the procedure carried out in traditionally making such blood pressure measurement.

An example of a prior art automatic applicator is found in U.S. Pat. No. 3,935,984 which shows a cuff applicator in which an encircling flexible band is provided with an inflatable chamber disposed within the band over a portion of its interior. The band is adapted to be automatically reduced in diameter by virtue of a cable adapted to force a free end of the band into overlapping relationship with itself to reduce the opening into which the subject's arm has been placed until the inflatable chamber is brought into firm engagement with the subjects arm and the encircling band has occluded blood flow through the arm of the subject. Since the pressure surges within the inflatable chamber are produced by an engagement between the arm of the subject and the inflatable chamber, and since this differs from that existing between an inflatable cuff entirely encircling the arm as in traditional methods, some variations between readings obtained based on such cuff pressure readings and the traditional clinical data could occur.

It is therefore an object of the present invention to provide an automatic applicator arrangement for such blood pressure measurement cuff which resembles closely the situation existing in traditional blood pressure measurement procedures.

SUMMARY OF THE INVENTION

This and other objects of the present invention which will become apparent upon a reading of the following specification and claims is accomplished by an arrangement including a rotary member consisting of a rotatable drum within which is supported an inflatable pressure cuff, which is adapted to be encircled about the body member of a subject upon rotation of the drum so as to automatically apply the pressure cuff. The encirclement is produced by an arrangement restraining one end of the cuff against movement of the drum while the other end is adapted to be carried about the subjects body member by rotation of the drum by virtue of a connection with a flexible element passing about the periphery of the drum with a spring arrangement allowing extension of the element as the cuff is wound upon the limb of the subject. The rotary drum is supported between the end plates having openings therein which provide for entrance of the subject's forearm to properly position the same with respect to the extended cuff prior to encirclement, the end plates also providing a rotational support for the rotatable drum.

DETAILED DESCRIPTION

In the following detailed description certain specific terminology will be employed for the sake of clarity and a specific embodiment described in accordance with the requirements of 35 USC 112 but it is to be understood that this is not intended to be limiting and the invention should not be so construed inasmuch as many variations are possible within the scope of the appended claims.

Figure 1:
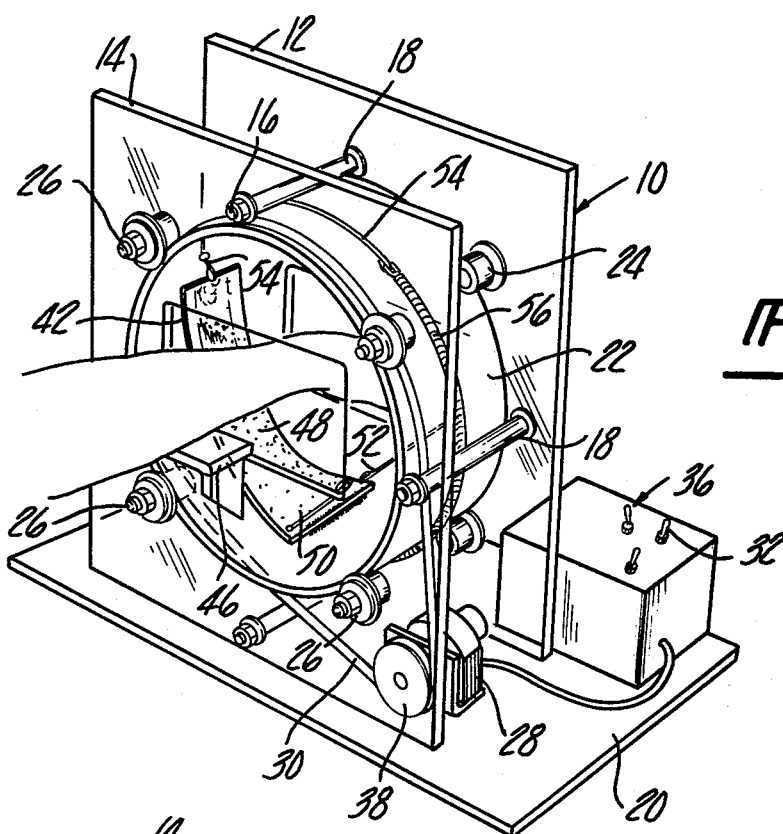
FIG. 1 is a perspective view of an automatic applicator apparatus according to the present invention.
Figure 2:
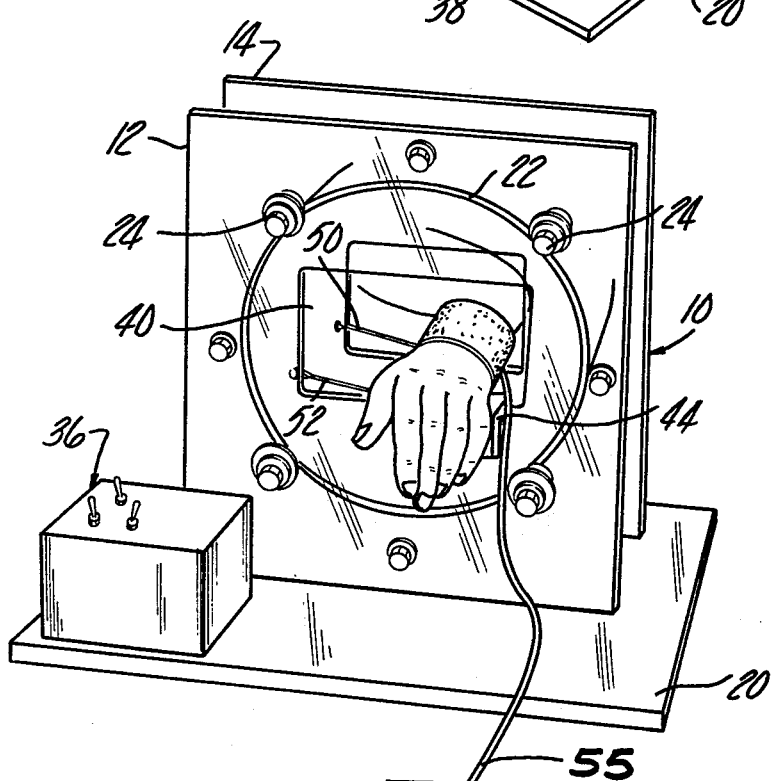
FIG. 2 is a perspective view of the applicator apparatus according to the present invention taken from another point of view.
Figure 6:
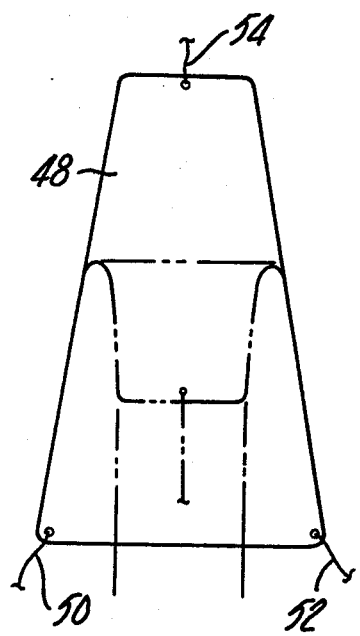
FIG. 6 is a perspective view of the cuff partially folded to show the relationship of the ties.

Referring to the drawings and particularly to FIGS. 1 and 2, the automatic applicator arrangement 10 includes a pair of stationary end plates 12 and 14 secured together by means of bolts 16 passing through spacer tubes 18, the combined assemblage being secured to a base surface 20. Rotatably supported between the end plates 12 and 14 is a rotary member consisting of a drum 22 rotatably supported by a plurality of rollers 24 and 26 supported by each end plate 12 and 14 respectively and engaging the outer surface of the rotatable drum 22 such as to allow rotation thereof. The drum 22 is adapted to be rotated on the rollers 24 and 26 by virtue of an electric motor 28 and a drive band 30 rotated thereby, with a power source 32 including control switching 36 provided to control the rotation of the drum 22. In addition, limit switches associated with a drive pulley 38 or alternatively the drum surface (not shown) would normally be provided to automate operation of the device i.e., by being adapted to control the electric motor 28 in order to detect the initial and fully wound condition of the drum rotation.

Each end plate 12 and 14 has an opening 40 and 42 respectively which allows insertion or entrance of the subject's arm so as to be passed through the interior of the drum 22. A pair of supports 44 and 46 respectively are provided to support the subject's limb and to locate the same at the proper location within the drum 22 which extends about the supports 44 and 46 for engagement with an inflatable flexible cuff 48 also disposed within the interior of the drum 22 shown in FIG. 1 in the extended or unwound condition.

The flexible cuff 48 is disposed opposite the subject's arm in the extended position. One end of the cuff in the extended position is restrained against movement relative the stationary end plates 12 and 14 by virtue of a pair of ties 50 and 52 secured to the outer edges of the one end of the flexible cuff 48. The position of the points of affixation of the ties 50 and 52 as well as the length thereof is selected such that the end of the cuff so restrained just engages the subject's arm upon rotation of the drum 22 as will be described hereinafter in further detail. The outer end of the flexible cuff 48 extends about the interior of the drum 22 and is adapted to be carried therewith during rotation of the drum by virtue of a flexible element 54 affixed to the other end of the flexible cuff 48 at a lateral point interiorly of the ties 50 and 52 on the flexible cuff 48 for a purpose to be described hereinafter.

The flexible element 54 passes out the wall of the drum 22 and extends about the periphery thereof for a short length. Affixed to the end of the flexible element 54 so disposed on the exterior of the carrier drum 22, is a garter spring 56 having one end attached to the flexible element 54 and the other end fastened to the drum 22. Thus as the drum rotates, the end of the flexible cuff 48 secured to the flexible element 54 is carried about the limb of the subject while the one end of the cuff 48 is restrained from moving together with the drum 22.

Figure 3:
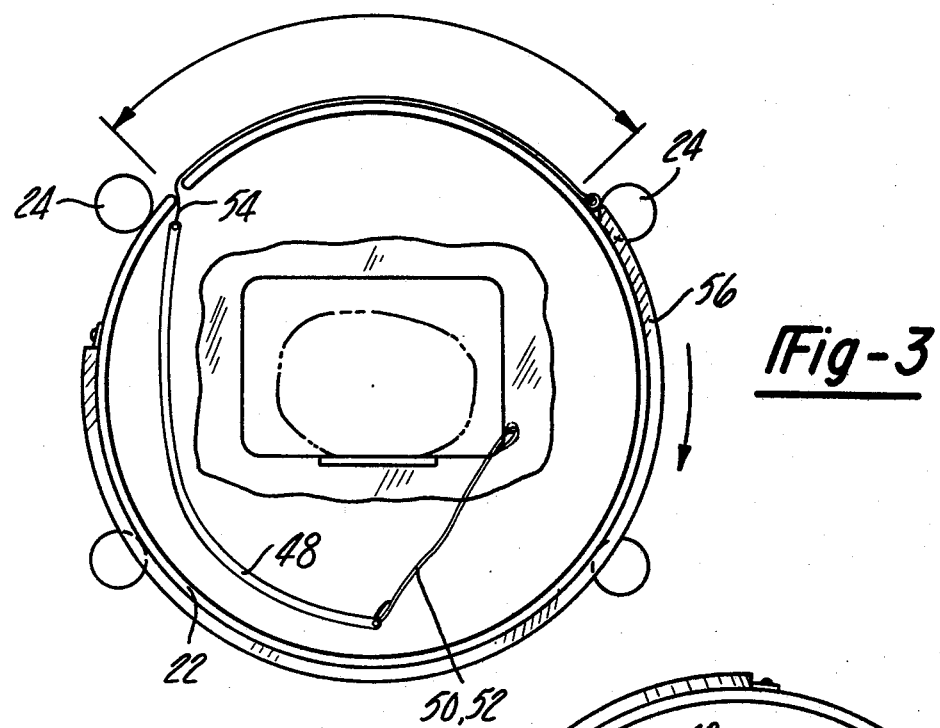
FIGS. 3 through 5 are diagrammatic representations of the drum, cuff and arm showing the relative movement of the parts as the encirclement is carried out by rotation of the carrier drum.
Figure 4:
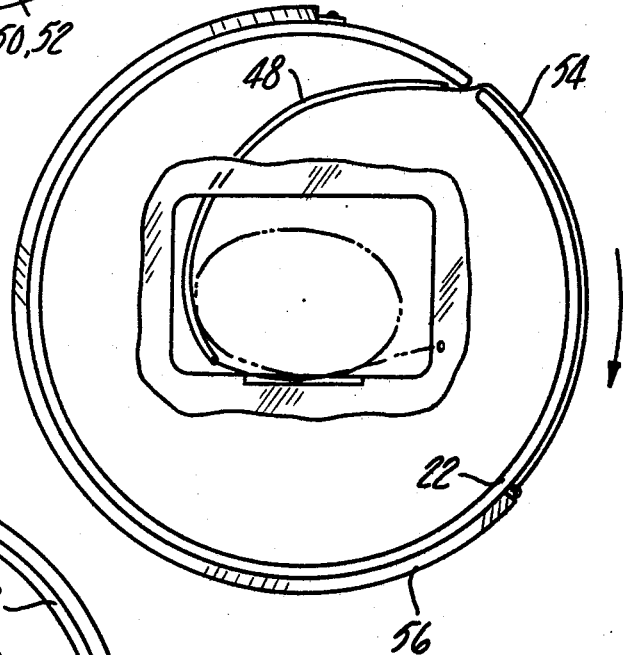
Figure 5:
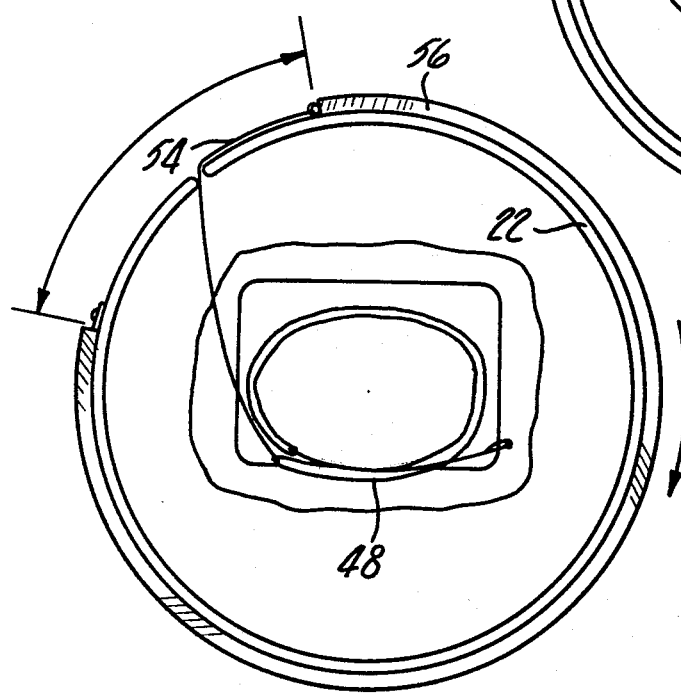

The encirclement process can be best understood by reference to FIGS. 3 through 5 which show the encirclement process in diagramatic form in various stages thereof. In FIG. 3 the cuff 22 is in the extended position initially with one end secured by the ties 50, 52 restrained from movement, the other end of the cuff 48 being held by virtue of its connection with the flexible element 54. Upon rotation of the drum 22 clockwise as viewed in FIG. 4 the cuff 48 is initially lifted such that the one end of the cuff is brought into contact with the subject's arm, the ties 50, 52 extending roughly tangentially in the taut position as shown. Upon continued rotation of the drum 22, the flexible cuff 48 is caused to encircle the arm of the subject until an overlap condition of the ends of the flexible cuff 48 is produced as shown in FIG. 5. As can be seen in FIG. 5, as the flexible cuff 48 encircles the subject's arm or forearm, the end secured to the flexible element 54 moves radially inward and the extension of the garter spring 56 allows the flexible element 54 to extend during the encirclement process while applying a more or less constant tension thereof to snugly enclose the subject's forearm. The degree of rotation of the drum 22 is sufficient such that some radially inward pressure is applied to the overlap portions of the flexible cuff to allow a pressure sensitive securement means to secure together the overlapped ends of the flexible cuff 48. Such material as the "Velcro" fastener material is suitable for this purpose.

The cuff would then be inflated via a fluid tube 55, the fluid communication with the interior of the cuff 48 and connected to a source of pneumatic pressure with the appropriate gaging equipment, etc., being associated therewith.

As will be apparent from an examination of FIGS. 3 through 5, in order for the encirclement process to be carried out the other end of the cuff secured to the flexible element 54 must pass between the ties 50, 52 and the reason for the outboard location of the securement locations to the one edge of the flexible cuff becomes apparent, since the central flexible element may thusly pass through between the ties 50, 52 during the encirclement process by virtue of being supported on the drum 22. The electric motor 28 may then be turned off, since the garter spring 56 will in the position shown in FIG. 5 tend to maintain the rotative position of the drum 22 as flexible cuff 48 has been looped entirely about the subject's forearm so that the ties 50, 52 and the flexible element are oppositely extending as shown in FIG. 5. The garter spring 56 is designed to maintain a constant tension such that coupled with the use of Velcro material an appropriate tightness is maintained. After completion of the pressure analysis, reverse rotation of the drum 22 takes place to peel the Velcro material apart, and unwind the flexible cuff back to the initial position, the tension of the garter spring 56 aiding to reposition the flexible cuff by radial withdrawal of the flexible element 54.

It can thus be appreciated that the applicator according to the present invention will substantially reproduce the clinical conditions existing in making traditional blood pressure measurement inasmuch as the end results are the same. It can further be appreciated that the present invention provides this result with a relatively simple apparatus adaptable to many applications and having relatively trouble free components therefor adapted for incorporation into coin operated apparatus, etc., and the like which must be relatively maintenance and trouble free.

The embodiments of the invention in which an exclusive property or privilege is claimed are defined as follows:

1. An arrangement for encircling a body member with an inflatable flexible cuff comprising:
   an inflatable flexible cuff adapted to be extended with separated ends;
   support means for positioning a body member with respect to said flexible cuff;

means for disposing said cuff in an extended position opposite a body member positioned by said support means;

means for restraining movement of one end of said flexible cuff with respect to said support means;

means for moving the other end of said flexible cuff about a body member supported by said support means to overlap said one end whereby said flexible cuff encircles said body member, said means for moving including a rotary member extending about said support means and said flexible cuff and connected to said other end of said cuff and further including means rotatably supporting said rotary member for rotation about said support means and said flexible cuff; and means for inflating said flexible cuff after rotation of said rotary member to encircle said body member.

2. The arrangement according to claim 1 wherein said means restraining said one end of said cuff includes a pair of elements secured to said one end of said cuff at locations at the outer edge of said one end of said cuff and wherein said means moving said other end of said cuff includes an element secured to said other end of said cuff at a lateral location intermediate said spaced locations whereby said other end of said cuff may be drawn between said elements secured to said one end of said cuff to overlap said one and the other ends of said cuff.

3. The arrangement according to claim 1 further includes means securing said one end and the other end of said cuff together upon bringing said one and the other end of said cuff into overlapping engagement.

4. The arrangement according to claim 1 wherein said connection of said other end of said cuff to said rotary member includes an element carried by said rotary member and secured to said other end of said cuff.

5. The arrangement according to claim 4 further including means allowing extension of said element from said rotary member as said rotary member is rotated to cause said cuff to encircle said body member.

6. The arrangement according to claim 5 further including means maintaining substantially constant tension on said element as said element extends.

7. The arrangement according to claim 1 wherein said rotary member comprises a drum and means for rotating said drum and wherein said cuff is disposed within said drum.

8. The arrangement according to claim 7 wherein said means rotating said drum includes a belt drive extending about said drum.

9. The arrangement according to claim 7 wherein said connection of said cuff to said drum includes an element carried by said drum and secured to said other end of said cuff.

10. The arrangement according to claim 9 further including means allowing extension of said element as said drum is rotated to produce encirclement of said body member.

11. The arrangement according to claim 10 wherein said element is flexible and extends about the exterior of said drum and extends into the interior of said drum in order to be secured to said other end of said cuff.

12. The arrangement according to claim 11 wherein said means allowing extension of said element includes spring means connected to said element.

13. The arrangement according to claim 12 wherein said spring means comprises a garter spring means carried by said drum and partially extending about the periphery of said drum.

14. The arrangement according to claim 1 wherein said means supporting said rotary member includes a pair of end plates between which said rotary member is supported, said end plates being formed with openings allowing passing said body member through said end plates and into the interior of said rotary member.

15. The arrangement according to claim 14 wherein said support means is affixed to said end plates to locate said body member with respect to said cuff.

16. The arrangement according to claim 14 wherein said means restraining said one end of said cuff includes a pair of flexible elements, one each connected at one end to a respective end plate and at the other end to said one end of said cuff at the outer edge thereof.

17. The arrangement according to claim 16 wherein said pair of flexible elements are located and are of a length to extend approximately tangentially to said body member upon rotation of said rotary member sufficient to produce contact of said one end of said cuff with said body member.

18. The arrangement according to claim 17 wherein said connection between said other end of said cuff and said rotary member comprises a flexible element carried by said rotary member and extending substantially oppositely to said pair of flexible elements upon rotation of said rotary member sufficient to encircle said body member.

19. The arrangement according to claim 16 wherein said connection between said other end of said cuff and said rotary member comprises a flexible element carried by said rotary member and includes means securing said flexible element to said other end of said cuff at a point intermediate the lateral edges of said cuff.

* * * * *